United States Patent
Hoffmann et al.

(10) Patent No.: US 7,153,846 B2
(45) Date of Patent: Dec. 26, 2006

(54) BENGAMIDE DERIVATIVES, PROCESS FOR PREPARING THEM, AND THEIR USE

(75) Inventors: Holger Hoffmann, Heppenheim (DE); Sabine Haag-Richter, Frankfurt (DE); Michael Kurz, Hofheim (DE); Heiko Tietgen, Mainz (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 10/971,228

(22) Filed: Oct. 22, 2004

(65) Prior Publication Data
US 2005/0171089 A1    Aug. 4, 2005

Related U.S. Application Data

(60) Provisional application No. 60/552,671, filed on Mar. 12, 2004.

(30) Foreign Application Priority Data
Oct. 24, 2003    (DE) ................. 103 49 669

(51) Int. Cl.
C07D 223/12    (2006.01)
A61K 31/55    (2006.01)
A61P 35/00    (2006.01)

(52) U.S. Cl. .................. 514/212.03; 540/526; 540/527

(58) Field of Classification Search ............... 540/526, 540/527; 514/212.03
See application file for complete search history.

(56) References Cited

FOREIGN PATENT DOCUMENTS

JP    2004-262793 A    9/2004

WO    WO 01/85697    11/2001

OTHER PUBLICATIONS

Adamczeski et al. (Journal of the American Chemical Society (1989), 111(2), 647-654).*
Groweiss, et al., Cytotoxic Metabolites from an Australian Collection of the Sponge, J. Nat. Prod.; 1999; 62; pp. 1691-1693.
Kinder, et al., Synthesis and Antitumor Activity of Ester-Modified Analogues of Bengamide B, J. Med. Chem.; 2001; 44; pp. 3691-3699.
Thale, et al., Bengamides Revisited: New Structures and Antitumor Studies, J. Org. Chem.; 2001; 66; pp. 1733-1741.

* cited by examiner

*Primary Examiner*—Bruck Kifle
(74) *Attorney, Agent, or Firm*—James Bolosak

(57) ABSTRACT

The present invention relates to bengamide derivatives which are formed, during fermentation, by the microorganism *Myxococcus virescens* ST200611 (DSM 15898), to their use for treating cancer diseases, to pharmaceuticals which comprise bengamide derivatives, to a process for preparing bengamides of the formula (V) and to the microorganism *Myxococcus virescens* ST200611 (DSM 15898)

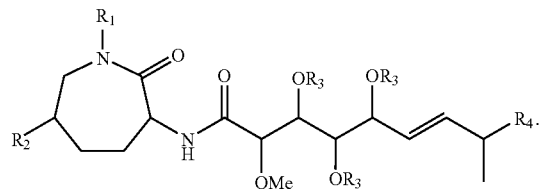

30 Claims, No Drawings

BENGAMIDE DERIVATIVES, PROCESS FOR PREPARING THEM, AND THEIR USE

RELATED APPLICATION DATA

This application claims the benefit of priority from German Patent Application No. 10349669.6-44, filed Oct. 24, 2003, as well as the benefit of U.S. Provisional Application No. 60/552,671, filed Mar. 12, 2004; which applications are hereby incorporated by reference.

BACKGROUND OF THE INVENTION

1. Field of the Invention

Cancer is a disease of humans and animals which is for the most part fatal and which is caused by the uncontrolled growth of endogenous cells. Cancer is the term for the formation of malignant tumors (malignomas) and of neoplasms (tumors or carcinomas) or for the malignant degeneration and disturbed maturation of white blood cells (leukemia, blood cancer). Cancer cells or tumor cells arise as the result of the transformation of endogenous cells. The malignancy of the cancer cell is expressed in the autonomy of its growth, that is in the ability of the cell to grow in an uninhibited manner and without being fitted into the structure of the organs and also to grow in an infiltrating manner, thereby destroying tissue. The formation of disseminations (metastases) at a distance from the tumor, after tumor cells have been spread by way of the blood or the lymph, is a sure sign of malignancy. Cancer is one of the most frequent causes of death in humans and there is therefore a great need for methods and means for curing or treating malignant degenerations.

Aside from the, if possible radical, surgical removal of the tumor, the possibilities for treating malignant tumors include radiological therapy using X-rays, α-rays, β-rays and γ-rays, immunotherapy and chemotherapy. At present, immunotherapy can only be used to a limited extent. The chemotherapy of tumors is understood as meaning the administration of cell poisons (cytostatic agents) for treating tumors and tumor cells which remain, usually following local surgical treatment or irradiation. These substances interfere specifically in certain processes in cell division, which means that tissues containing a high proportion of dividing cells, such as rapidly growing tumor tissues, react more sensitively. The cytostatic agents which are used are alkylating compounds, such as cyclophosphamide, antimetabolites, such as methotrexate, alkaloids, such as vincristine, and antibiotics, such as daunomycin or adriamycin. However, due to massive side-effects, all these agents suffer from severe disadvantages, such that the death of the affected patient is only delayed and not averted. Furthermore, the degenerate (cancer) cells develop resistances to the agents which are used; while the medicaments which are being used at the time then no longer have any cytostatic effect, they are still toxic as a consequence of the side-effects. In addition, it has been found that the efficacy achieved by using cytostatic agents in combination or in sequence exceeds that achieved by using a single cytostatic agent (monotherapy) and, as a result, it is possible that the substantial side-effects are not additive in connection with polychemotherapy. For all these reasons, novel chemotherapeutic agents are urgently required and are therefore being sought world-wide.

2. Description of the Art

The first examples of bengamides were bengamides A and B, which are dodecanoyl-substituted on the caprolactam ring and which were isolated from the sea sponge Jaspis cf. Coriacea (family Coppatiidae, order Choristida B Astrophorida) (Adamczewski et al., J. Org. Chem. 1986, 51, 4497–4498) and reported to be biotoxic to eukaryotic cells, nematodes and bacteria.

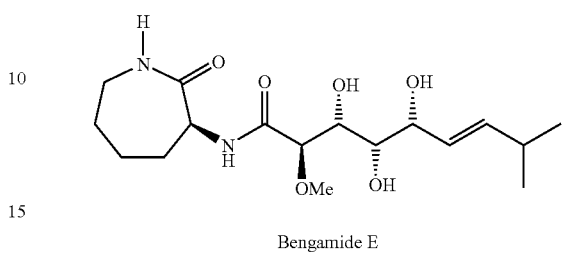

Bengamide E and its N-methylated derivative bengamide F are examples of bengamide derivatives which have been demonstrated to possess antitumor activity. Bengamide E inhibits cell proliferation by stopping cell division at the G1/S restriction point and in the G2/M phase of the cell cycle. Bengamide B derivatives inhibit the proliferation of MDA-MB-435 breast cancer cells (Kinder et al., J. Med. Chem. 2001, 44, 3692–3699).

A feature shared in common by the known bengamide derivatives is that they have been isolated from sea sponges of the genus Jaspis sp. or Pachastrissa sp. (Thale et al., J. Org. Chem. 2001, 66, 1733–1741).

SUMMARY OF THE INVENTION

It has now been found that the microorganism strain Myxococus virescens ST200611 (DSM 15898) is able to form novel bengamide derivatives which inhibit cell proliferation at low concentrations and are consequently suitable to be used for the treatment and/or prophylaxis of cancer diseases.

DETAILED DESCRIPTION OF THE INVENTION

The present invention relates to a compound of the formula (I),

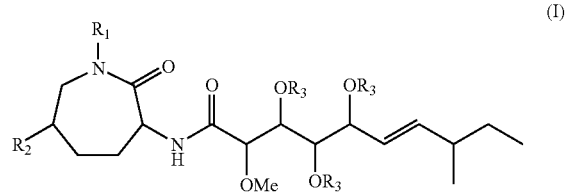

wherein
  $R_1$ is H or $(C_1-C_6)$-alkyl,
  $R_2$ is H or OH, and
  $R_3$ is H or $-C(=O)-(C_1-C_6)$-alkyl, or to a physiologically tolerated salt of a compound of the formula (I).

Independently of each other, $R_1$ is preferably H or methyl and $R_3$ is preferably H.

The invention preferably relates to a compound of the formula (I) in which $R_1$ is H or methyl, $R_2$ is H or OH, and $R_3$ is H.

($C_1$–$C_6$)-Alkyl is a straight-chain or branched alkyl group having 6 carbon atoms, for example methyl (Me), ethyl, n-propyl, iso-propyl, tert-butyl or n-hexyl, preferably methyl.

In addition, the invention relates to a compound of the formula (I) which is characterized by a compound of the formula (II)

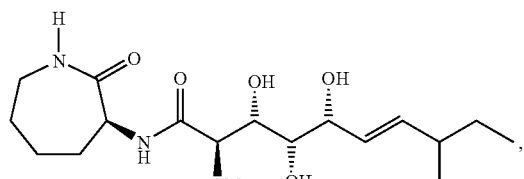

(II)

a compound of the formula (III)

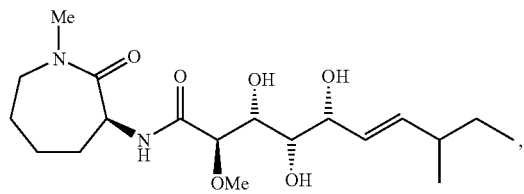

(III)

and a compound of the formula (IV)

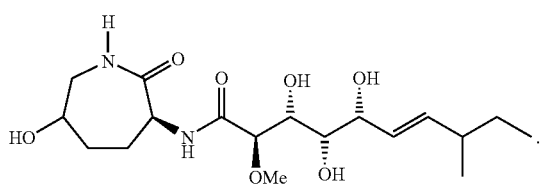

(IV)

The present invention furthermore relates to all obvious chemical equivalents of the compounds of the formula (I) according to the invention. These equivalents are compounds which exhibit only a slight chemical difference, and have the same pharmacological effect, or which are converted into the compounds according to the invention under mild conditions. Said equivalents also include, for example, salts, reduction products, oxidation products, esters, ethers, acetals or amides of the compounds of the formula (I) as well as equivalents which the skilled person can prepare using standard methods and, in addition to this, all the optical antipodes and diastereomers and all the stereoisomeric forms.

The invention also relates to a process for preparing a compound of the formula (V)

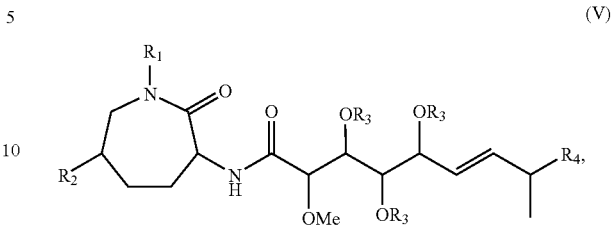

(V)

wherein $R_1$ is H or ($C_1$–$C_6$)-alkyl, $R_2$ is H or OH, $R_3$ is H or —C(=O)—($C_1$–$C_6$)-alkyl, and $R_4$ is methyl or ethyl, or to a physiologically tolerated salt of a compound of the formula (V), which comprises 1. the strain *Myxococcus virescens* ST200611 (DSM 15898), or one of its variants and/or mutants, being fermented under suitable conditions in a culture medium until one or more of the compounds of the formula (V) accrue(s) in the culture medium,
2. a compound of the formula (V) being isolated from the culture medium, and
3. the compound of the formula (V) being derivatized, where appropriate, and/or, where appropriate, being converted into a physiologically tolerated salt.

The invention preferably relates to a process for preparing a compound of the formula (V) where $R_4$ is ethyl. The product of such a process corresponds to a compound of the formula (I) as described above.

The invention particularly preferably relates to a process for preparing a compound of the formula (V) where, independently of each other, $R_1$ is H or methyl, $R_3$ is H and $R_4$ is ethyl.

In addition, the invention relates to a process for preparing a compound of the formula (II), a compound of the formula (III) and a compound of the formula (IV) as well as the bengamide derivatives E and F.

Unless otherwise indicated, the chiral centers in the compounds of the formula (I) and (V) can be present in the R configuration or in the S configuration. The invention relates both to the optically pure compounds and to stereoisomeric mixtures, such as enantiomeric mixtures and diastereomeric mixtures.

Physiologically tolerated salts of compounds of the formula (I) and (V) are understood as being both their organic salts and their inorganic salts, as are described in Remington's Pharmaceutical Sciences (17th edition, page 1418 (1985)). Because of their physical and chemical stability and their solubility, sodium, potassium, calcium and ammonium salts are preferred, inter alia, for acid groups; salts of hydrochloric acid, sulfuric acid or phosphoric acid, or of carboxylic acids or sulfonic acids, such as acetic acid, citric acid, benzoic acid, maleic acid, fumaric acid, tartaric acid and p-toluenesulfonic acid, are preferred, inter alia, for basic groups.

The culture medium is a nutrient solution or a solid medium containing at least one customary carbon source and nitrogen source as well as the customary inorganic salts.

If hydroxylysine is added to the culture medium, the strain *Myxococcus virescens* ST200611 (DSM 15898) produces a compound of the formula (V) in which $R_2$ is OH as a result of digesting hydroxylysine.

One part of the subject matter of the present invention is therefore a process for preparing a compound of the formula (V) as described above where $R_2$ is OH and where the culture medium in step 1 contains hydroxylysine.

The process according to the invention can be used for fermenting on a laboratory scale (milliliter to liter scale) and for fermenting on an industrial scale (cubic meter scale).

Suitable carbon sources for the fermentation are assimilable carbohydrates and sugar alcohols, such as glucose, lactose, sucrose or D-mannitol, as well as carbohydrate-containing natural products, such as malt extract or yeast extract. Examples of nitrogen-containing nutrients are amino acids; peptides and proteins and also their breakdown products, for example casein, peptones or tryptones; meat extracts; yeast extracts; gluten; ground seeds, for example from corn, wheat, beans, soya or the cotton plant; distillation residues from producing alcohol; meat meals; yeast extracts; ammonium salts; nitrates. Preference is given to the nitrogen source being one or more peptide(s) which has/have been obtained synthetically or biosynthetically. Examples of inorganic salts are chlorides, carbonates, sulfates or phosphates of the alkali metals, the alkaline earth metals, iron, zinc, cobalt and manganese. Examples of trace elements are cobalt and manganese.

Conditions which are suitable for forming the bengamides according to the invention are as follows: the bengamides according to the invention are preferably formed in a culture medium which contains from 0.05 to 5%, preferably from 0.1 to 2.5%, yeast extract; from 0.2 to 5.0%, preferably from 0.1 to 2%, casitone; from 0.02 to 1.0%, preferably from 0.05 to 0.5%, $CaCl_2 \times 2\ H_2O$; from 0.02 to 1.5%, preferably from 0.05 to 0.7%, $MgSO_4 \times 7\ H_2O$ and from 0.00001% to 0.001% cyanocobalamin. The percentage values which are given are in each case based on the weight of the total nutrient solution.

The microorganism is cultured aerobically, that is, for example, submerged while being shaken or stirred in shaking flasks or fermenters, or on solid medium, where appropriate while air or oxygen is being passed in. The microorganism can be cultured in a temperature range of from about 18 to 35° C., preferably at from about 20 to 32° C., in particular at from 27 to 30° C. The pH range should be between 4 and 10, preferably between 6.5 and 7.5. The microorganism is generally cultured under these conditions for a period of from 2 to 10 days, preferably of from 72 to 168 hours. The micro organism is advantageously cultured in several steps, i.e. one or more preliminary cultures are initially prepared in a liquid nutrient medium, with these preliminary cultures then being inoculated into the actual production medium, i.e. the main culture, for example in a ratio by volume of from 1:10 to 1:100. The preliminary culture is obtained, for example, by inoculating the strain, in the form of vegetative cells or fruiting bodies, into a nutrient solution and allowing it to grow for from about 20 to 120 hours, preferably for from 48 to 96 hours. Vegetative cells and/or fruiting bodies can be obtained, for example, by allowing the strain to grow for from about 1 to 15 days, preferably for from 4 to 10 days, on a solid or liquid nutrient substrate, for example yeast agar.

A bengamide derivative of the formula (V) is isolated or purified from the culture medium using known methods and taking account of the chemical, physical and biological properties of the natural substances. HPLC was used to test the concentrations of the respective bengamide derivatives in the culture medium or in the individual isolation steps, with the quantity of the substance formed expediently being compared with a calibration solution.

For the isolation, the culture broth or the culture together with the solid medium is lyophilized, after which the bengamide derivatives are extracted from the lyophilizate using an organic solvent, for example methanol or 2-propanol. The organic solvent phase contains the natural substances according to the invention; it is concentrated, where appropriate, in vacuo and subjected to further purification.

The further purification of one or more compounds according to the invention is effected by chromatography on suitable materials, preferably, for example, on molecular sieves, on silica gel, on aluminum oxide, on ion exchangers or on adsorber resins or on reversed phases (RPs). This chromatography is used to separate the bengamide derivatives. The bengamide derivatives are chromatographed using buffered aqueous solutions or mixtures of aqueous and organic solutions.

Mixtures of aqueous or organic solutions are understood as being all water-miscible organic solvents, preferably methanol, 2-propanol or acetonitrile, at a concentration of from 5 to 95% solvent, preferably from 5 to 40% solvent, or else all buffered aqueous solutions which are miscible with organic solvents. The buffers which are to be used are the same as specified above.

The bengamide derivatives are separated, on the basis of their differing polarities, by means of reversed phase chromatography, for example on MCI® (adsorber resin from Mitsubishi, Japan) or Amberlite XAD® (TOSOHAAS), or on other hydrophobic materials, for example on RP-8 or RP-18 phases. In addition, the separation can be effected by means of normal-phase chromatography, for example on silica gel, aluminum oxide and the like.

The bengamide derivatives are chromatographed using buffered, basic or acidified aqueous solutions or mixtures of aqueous solutions with alcohols or other water-miscible organic solvents. Preference is given to using acetonitrile and methanol as organic solvent.

Buffered, basic or acidified aqueous solutions are understood as being, for example, water, phosphate buffer, ammonium acetate and citrate buffer at a concentration of up to 0.5 M, as well as formic acid, acetic acid, trifluoroacetic acid, ammonia and triethylamine, or all commercially available acids and bases known to the skilled person, preferably at a concentration of up to 1%. In the case of buffered aqueous solutions, particular preference is given to 0.1% ammonium acetate.

The chromatography was carried out using a gradient which began with 100% water and ended with 100% solvent; the chromatography was preferably run with a linear gradient of from 5 to 95% acetonitrile.

Alternatively, it is also possible to carry out a gel chromatography or chromatography on hydrophobic phases. The gel chromatography is carried out on polyacrylamide gels or copolymer gels, such as Biogel-P 2® (Biorad) or Fractogel TSK HW 40® (Merck, Germany). The sequence of the abovementioned chromatographic steps can be reversed.

Insofar as bengamides are present as diastereomers, they can be separated using known methods, for example by means of separation using a chiral column.

The derivatization of the OH groups in the side chain of the compounds of the formulae (I) and/or (V) ($R_3$ is in each case H) to give an acyl group ($R_4$ is in each case $-C(=O)-(C_1-C_6)$-alkyl) is effected using methods which are known per se (J. March, Advanced Organic Chemistry, John Wiley & Sons, 4th edition, 1992), for example by means of reaction with an acid anhydride. For example, Adamczeski et al., J. Am. Chem. Soc. 1989, 111, 647–654 describe the reaction with acetic anhydride to give a compound of the formula (I) and/or (V) in which $R_3$ is —C(=O)—$CH_3$.

The alkylation of the NH group in the caprolactam ring of a compound of formula (I) or (V) ($R_1$ is in each case H) is likewise effected using methods which are known per se (J. March, Advanced Organic Chemistry, John Wiley & Sons, 4th Edition, 1992), for example by reaction with $Me_2CO_3$ or $Me_2SO_4$, to prepare the corresponding N-methylated derivatives, or by reaction with ($C_1$–$C_6$)-alkyl bromide in the presence of a base.

An isolate of the microorganism strain *Myxococcus virescens* ST200611 was deposited in the Deutschen Sammlung von Mikroorganismen und Zellkulturen [German Collection of Microorganisms and Cell Cultures] GmbH (DSMZ), Mascheroder Weg 1B, 38124 Braunschweig, Germany, in accordance with the rules of the Budapest treaty, on 11.09.2003 under the following number: DSM 15898.

The vegetative cells of the strain DSM 15898 have the rod form which is characteristic for *Myxococcus virescens*. On solid nutrient substrates, *Myxococcus virescens* ST200611 (DSM 15898) forms orange-yellow fruiting bodies which contain round myxospores.

Instead of the strain *Myxococcus virescens* ST200611 (DSM 15898), it is also possible to use its mutants and/or variants which synthesize one or more of the compounds according to the invention.

A mutant is a microorganism in which one or more genes in the genome has/have been modified, with the gene, or the genes, which is/are responsible for the ability of the organism to produce the compound according to the invention remaining functional and heritable.

Such mutants can be produced, in a manner known per se, using physical means, for example irradiation, as with ultraviolet rays or X-rays, or chemical mutagens, such as ethyl methanesulfonate (EMS); 2-hydroxy-4-methoxybenzophenone (MOB) or N-methyl-N'-nitro-N-nitrosoguanidine (MNNG), or as described by Brock et al. in "Biology of Microorganisms", Prentice Hall, pages 238–247 (1984).

A variant is a phenotype of the microorganism. Microorganisms have the ability to adapt to their environment and therefore exhibit highly developed physiological flexibility. All the cells of the microorganism are involved in the phenotypic adaptation, with the nature of the change not being genetically conditioned and being reversible under altered conditions (H. Stolp, Microbial ecology: organism, habitats, activities. Cambridge University Press, Cambridge, GB, page 180,1988).

Screening for mutants and/or variants which synthesize one or more of the compounds according to the invention takes place in accordance with the following scheme:
lyophilizing the fermentation medium;
extracting the lyophilizate with an organic solvent
extracting the compound from the culture filtrate using solid phases
analyzing by means of HPLC or TLC or by testing the biological activity.

The fermentation conditions which have been described apply for *Myxococcus virescens* ST200611 (DSM 15898) and for mutants and/or variants thereof.

The present invention also relates to the use of the microorganism *Myxococcus virescens* ST200611 (DSM 15898), or of a mutant and/or variant, for preparing a compound of the formula (V), in particular a compound of the formula (IV), or a physiologically tolerated salt thereof, as described above.

A test which is based on determining the intracellular concentration of ATP is employed for detecting the inhibition of cell proliferation. It is possible to use known tumor cell lines such as Hep-G2 and Colo205. In this test, the ATP content of metabolically active cells serves, in a luciferase reaction, as a measure of the number of living cells.

The compounds of the formula (II)–(VI) were used in the test in a single dose of 0.3–40 μM and a dose dependency given as a TC50 value, with (IIA) and (IIB) in each case denoting a diastereomer of the compound of the formula (II):

TABLE 1

Activity of the bengamides in a cell proliferation test, expressed as TC50 value in μM

| Compound | Hep-G2 | Colo 205 |
| --- | --- | --- |
| (II) | 16 | 27 |
| (IIA) | 17 | 33 |
| (IIB) | 6 | 10 |
| (III) | 9 | 15 |
| (IV) | >40 | 42 |
| Bengamide E | 36 | 46 |
| Bengamide F | 27 | 33 |

The invention therefore also relates to the use of the compound of the formula (I) or of a physiologically tolerated salt thereof as a pharmaceutical in human or animal medicine, in particular for the treatment and/or prophylaxis of cancer diseases. The invention preferably relates to the use of a compound of the formula (I), or of a physiologically tolerated salt, for treating breast cancer, intestinal cancer, stomach cancer, liver cancer, brain tumors, ovarial tumors, esophageal cancer, renal cancer and muscle cell carcinoma, in particular carcinoma of the head and neck muscles.

In addition, the present invention relates to a pharmaceutical having a content of at least one compound of the formula (I) or of a physiologically tolerated salt thereof, with it being possible for the compound or the compounds of the formula (I) to be administered as such or, preferably, to be present in a mixture with one or more of the customary, pharmacologically suitable carrier substances or auxiliary substances.

The compounds according to the invention are stable in the solid state and in solutions in a pH range of between 2 and 9, in particular 5 and 7, and, as a consequence, can be incorporated into customary galenic preparations.

While the pharmaceuticals according to the invention can be administered orally or parenterally, a rectal use is also possible in principle. Examples of suitable solid or liquid galenic preparation forms are granules, powders, tablets, sugar-coated tablets, (micro)capsules, suppositories, syrups, emulsions, suspensions, aerosols, drops or injectable solutions in ampoule form, as well as preparations giving a protracted release of active compound, in connection with whose preparation use is customarily made of pharmacologically suitable carrier substances or auxiliary substances, such as disintegrants, binders, coating agents, swelling agents, glidants, lubricants, flavoring substances, sweeteners or solubilizers, for example magnesium carbonate, titanium dioxide, lactose, mannitol and other sugars, talc, milk protein, gelatin, starch, vitamins, cellulose and its derivatives, animal or vegetable oils, polyethylene glycols and solvents, such as sterile water, alcohols, glycerol and polyhydric alcohols.

Where appropriate, the dosage units for oral administration can be micro-encapsulated in order to delay release or to extend it over a relatively long period, for example by means of coating or embedding the active compound in particle form in suitable polymers, waxes or the like.

Preference is given to producing and administering the pharmaceutical preparations in dosage units, with each unit containing, as the active constituent, a defined dose of one or more compounds of the bengamide derivatives of the formula (I). In the case of solid dosage units such as tablets, capsules and suppositories, this dose can be up to about 500 mg, preferably, however, from about 0.1 to 200 mg, and, in the case of injection solutions in ampoule form, up to about 200 mg, preferably, however, from about 0.5 to 100 mg, per day.

The daily dose which is to be administered depends on the bodyweight, age, sex and condition of the mammalian subject. However, higher or lower daily doses may also possibly be appropriate. The daily dose can be administered both by means of once-only administration in the form of a single dosage unit, or else in several smaller dosage units, and by means of the multiple administration of subdivided doses at defined intervals.

The pharmaceuticals according to the invention are produced by bringing one or more of the compounds of the formula (I) according to the invention into a suitable form for administration, optionally together with one or more of the customary carrier substances or auxiliary substances.

The following examples are intended to explain the invention in more detail without limiting its scope in any way.

Unless otherwise indicated, percentage values refer to the weight and mixing ratios in the case of liquids refer to the volume.

EXAMPLE 1

Storing *Myxococcus virescens* ST200611 (DSM 15898) at −135° C.

An agar plate (1% fresh baker's yeast, 1% $CaCl_2 \times 2\ H_2O$, 20 mM HEPES, 0.00005% cyanocobalamin, 1.5% agar, pH 7.2) is inoculated with the strain *Myxococcus virescens* ST200611 (DSM 15898) and incubated at 30° C. for approx. 7 days. The cells in this surface culture are scratched off the agar surface using a sterile spatula, resuspended in 0.5 ml of casitone medium (1% casitone (Difco), 0.15% $MgSO_4 \times 7\ H_2O$, pH 7.0) and stored at −135° C.

EXAMPLE 2

Preparing a Preliminary Culture of *Myxococcus virescens* ST200611 (DSM 15898) in an Erlenmeyer Flask 100 ml of nutrient solution (1% fresh baker's yeast, 1% $CaCl_2 \times 2\ H_2O$, 20 mM HEPES, 0.00005% cyanocobalamin, pH 7.2) in a sterile 300 ml Erlenmeyer flask are inoculated with the strain *Myxococcus virescens* ST200611 (DSM 15898) and the culture is incubated for 4 days at 30° C. and 180 rpm on a rotating shaker. 5 ml of this preliminary culture are then used for preparing the main cultures.

EXAMPLE 3

Preparing a Liquid Main Culture of *Myxococcus virescens* ST200611 (DSM 15898)

A sterile 300 ml Erlenmeyer flask containing 100 ml of the following nutrient solution (0.5% yeast extract, 0.5% casitone, 0.1% $CaCl_2 \times 2\ H_2O$, 0.2% $MgSO_4 \times 7\ H_2O$, 0.00005% cyanocobalamin, pH 7.4) is inoculated with 5 ml of a preliminary culture (see example 2), or a culture which has grown on a fresh agar plate (1% fresh baker's yeast, 1% $CaCl_2 \times 2\ H_2O$, 20 mM HEPES, 0.00005% cyanocobalamin, pH 7.2, plus 1.5% agar), and incubated at 30° C. and 180 rpm on a shaker. The maximum production of the bengamides according to the invention is reached after 72–96 hours. A 72–96 hour-old submerged culture (inoculation quantity approx. 5–10%) from the same nutrient solution as described in example 2 is sufficient for inoculating from 10 to 200 l fermenters.

EXAMPLE 4

Preparing a Liquid Main Culture of *Myxococcus virescens* ST200611 (DSM 15898) while Feeding in Hydroxylysine for Producing the Bengamide Derivative (IV)

A sterile 300 ml Erlenmeyer flask containing 100 ml of the following nutrient solution (0.5% yeast extract, 0.5% casitone, 0.1% $CaCl_2 \times 2\ H_2O$, 0.2% $MgSO_4 \times 7\ H_2O$, 0.00005% cyanocobalamin and also 1 mM hydroxylysine pH 7.4) is inoculated with 5 ml of a preliminary culture from example 2 or a culture which has grown on a fresh agar plate (1% fresh baker's yeast, 1% $CaCl_2 \times 2\ H_2O$, 20 mM HEPES, 0.00005% cyanocobalamin, pH 7.2, plus 1.5% agar) and incubated at 30° C. and 180 rpm on a shaker. The maximum production of the bengamide derivative (IV) is reached after 72–96 hours. HPLC-MS was used for the analysis. A 72–96 hour-old submerged culture (inoculation quantity, approx. 5–10%) from the same nutrient solution as described in example 2 is sufficient for inoculating 10 to 200 l fermenters.

EXAMPLE 5

Preparing Bengamide Derivatives in a Fermenter

The 10 l and 30 l fermenters were operated under the following conditions:

| | | |
|---|---|---|
| Inoculum: | approx. 5% | approx. 9% |
| Fermenter: | 30 l | 10 l |
| Nutrient medium: | see example 2 | see example 2 |
| Incubation temperature: | 30° C. | 30° C. |
| Stirrer speed: | 112 rpm | 150 rpm |
| Aeration: | 8 l/min | 4 l/min |
| pH regulation: | from pH 7.8 to pH 7.5 | from pH 8.1 to pH 7.5 |
| $pO_2$ regulation: | none | none |

The pH was always regulated using 10% KOH or, respectively, 10% $H_2SO_4$. Foam formation can be suppressed by repeatedly adding Clerol FBA 265 (Cognis Deutschland GmbH). Maximum production is reached after approx. 72 to 96 hours.

EXAMPLE 6

Isolating Bengamide Derivatives (II) and (III), as Well as Bengamides E and F, from the Shaken Cultures of *Myxococcus virescens* ST200611 (DSM 15898)

After the *Myxococcus virescens* ST200611 (DSM 15898) fermentation had come to an end, the culture broth from example 3 (30 l culture broth), together with the biomass, was lyophilized and the lyophilizate was extracted with methanol (2×5 l). The methanol extract was reduced to 1.2 l under vacuum and then loaded onto a prepared column which was packed with approx. 1.5 liters of CHP-20P material (MCI® gel, 75–150μ, Mitsubishi Chemical Corporation). The column was eluted with 95% methanol. The column flow through (120 ml/min) was collected and reduced down to a volume of 1.5 l in vacuo.

EXAMPLE 7

Preseparating Bengamide Derivatives (II) and (III), and Also Bengamides E and F, by Means of RP-18 Chromatography 1.5 l of the solution obtained as described in example 6 were loaded onto a Phenomenex Luna® 10μ C18 (2) column (size: 50 mm×250 mm) possessing a Luna® 10μ C18 (2) precolumn (dimension: 21.2 mm×60 mm) and eluted (0.1% ammonium acetate, pH 4.6, adjusted with acetic acid) over 60 min using a gradient of from 5% to 95% acetonitrile in water. The flow rate was 150 m/min and the fraction size was 200 ml. Bengamides were present in fractions 5–9, 10–11 and 12–14.

EXAMPLE 8

Purifying Bengamide Derivatives (II) and (III) and Also Bengamides E and F

The individual fractions from example 7 were lyophilized and purified once more by means of HPLC on a Phenomenex Luna® 10 μm C18 (2) column (dimension: 21 mm×250 mm) possessing an XTerra®0 Prep MS C18 10 μm (Waters, dimension: 19×10 mm) precolumn. The column was eluted using a gradient of from 5% to 40% acetonitrile in water over 40 min (in the added presence of 0.1% ammonium acetate, pH 8.8, adjusted with triethylamine). The column flow through (50 ml/min) was collected in fractions (7.5 ml fractions in each case). Fractions 5–9 from example 7 contained the compound of the formula (III) and, after chromatography and lyophilization, yielded 86 mg of bengamide E (purity >95%). After chromatography, fractions 10–11 from example 7 yielded 145 mg of bengamide (II) (purity >95%, 70/30 diastereomeric mixture) and 5 mg of bengamide F (purity >95%). 35 mg of bengamide (III) (purity >95%) were obtained as a diastereomeric mixture, in a 75:25 ratio, from fractions 12–14 from example 7. The diastereomers are in each case the corresponding C-16 epimers.

EXAMPLE 9

Isolating the Hydroxybengamide (IV) from the Shaken Cultures of *Myxococcus virescens* ST200611 (DSM 15898)

After the *Myxococcus virescens* ST200611 (DSM 15898) fermentation had come to an end, the culture broth from example 5 (10 l of culture broth), together with the biomass, was lyophilized and the lyophilizate was extracted with methanol (2×3 l). The methanol extract was reduced under vacuum to 400 ml and then loaded onto a prepared column which had been packed with 0.6 liter of CHP-20P (MCI® gel, 75–150μ, Mitsubishi Chemical Corporation) material. The column was eluted with 5% to 95% methanol in water. The column flow through (100 ml/min) was collected in fractions over 60 min (0.5 min per fraction). The fractions containing the desired derivative (fractions 45–109) were pooled and reduced in vacuo down to a volume of 700 ml.

EXAMPLE 10

Prepurifying the Hydroxybengamide (IV) by Means of RP-18 Chromatography

The solution from example 9 was then loaded onto a Phenomenex Luna® 10μ C18 (2) column (size: 50 mm×250 mm) possessing a Phenomenex Luna® 10μ C18 (2) precolumn (dimension: 21.2 mm×60 mm) and eluted (0.1% ammonium acetate, pH 8.8, adjusted with triethylamine) using a gradient of from 5% to 40% acetonitrile in water over 60 min. The flow rate was 150 ml/min and the fraction size was 225 ml. Fraction 22 contained the desired bengamide derivative.

EXAMPLE 11

Purifying the Hydroxybengamide (IV)

Fraction 22 from example 10 was lyophilized and purified once again by means of HPLC on a Phenomenex Luna® 10 μm C18 (2) column (dimension: 21 mm×250 mm) possessing a Waters XTerra® Prep MS C18 10 μm precolumn (dimension: 19×10 mm). The column was eluted with a gradient of from 5% to 95% acetonitrile in water over 60 min (in the added presence of 0.1% ammonium acetate, pH 4.6, adjusted with acetic acid). The column flow through (50 ml/min) was collected in fractions (7.5 ml fractions in each case). The bengamide-containing fractions (fractions 26–28) were combined, desalted and freeze-dried. In connection with this, 7 mg of bengamide (IV) were obtained as a diastereomeric mixture in a ratio of 75:25.

EXAMPLE 12

Characterizing the Compound of the Formula (II)

Empirical formula: $C_{18}H_{32}N_2O_6$
Molecular weight: 372.47
Diastereomeric mixture: 75:25

TABLE 2

NMR-chemical shifts of bengamide (II), diastereomeric mixture, c = 3 mg/ml in DMSO, 300 K.

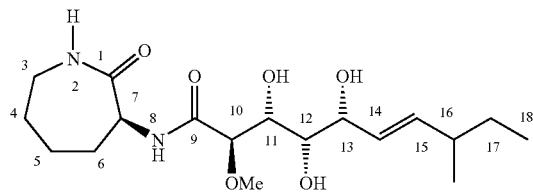

(II)

| Position | $^1$H | $^{13}$C |
|---|---|---|
| 1 | — | 173.99 |
| 2 | 7.91 | — |
| 3 | 3.19/3.06 | 40.56 |
| 4 | 1.74/1.20 | 28.75 |
| 5 | 1.87/1.64 | 27.55 |
| 6 | 1.87/1.36 | 30.72 |
| 7 | 4.39 | 51.27 |
| 8 | 7.78 | — |
| 9 | — | 169.61 |
| 10 | 3.69 | 81.60 |
| 10-OMe | 3.25 | 57.32 |
| 11 | 3.58 | 70.72 |
| 11-OH | 4.46 | — |
| 12 | 3.33 | 72.80 |
| 12-OH | 4.36 | — |
| 13 | 3.97 | 72.46 |
| 13-OH | 4.56 | — |
| 14 | 5.37 | 129.05 |
| 15 | 5.48 | 136.57 |
| 16 | 1.99 | 37.41 |
| 16-Me | 0.93 | 19.90 |
| 17 | 1.26 | 29.15 |
| 18 | 0.81 | 11.58 |

EXAMPLE 13

Characterizing the Compound of the Formula (III)

Empirical formula: $C_{19}H_{34}N_2O_6$
Molecular weight: 386.49
Diastereomeric mixture: 75/25

TABLE 3

NMR-chemical shifts of bengamide (III), diastereomeric mixture, c = 3 mg/ml in DMSO, 300 K.

| Position | $^1$H | $^{13}$C |
|---|---|---|
| 1 | — | 171.95 |
| 2 | 2.91 | 35.28 |
| 3 | 3.61/3.21 | 49.20 |
| 4 | 1.71/1.31 | 26.13 |
| 5 | 1.82/1.67 | 27.11 |
| 6 | 1.84/1.32 | 30.80 |
| 7 | 4.55 | 51.14 |
| 8 | 7.84 | — |
| 9 | — | 169.54 |
| 10 | 3.69 | 81.55 |
| 10-OMe | 3.25 | 57.28 |
| 11 | 3.57 | 70.69 |
| 11-OH | 4.45 | — |
| 12 | 3.33 | 72.77 |
| 12-OH | 4.37 | — |
| 13 | 3.97 | 72.47 |
| 13-OH | 4.56 | — |
| 14 | 5.37 | 129.04 |
| 15 | 5.48 | 136.58 |
| 16 | 1.99 | 37.41 |
| 16-Me | 0.93 | 19.89 |
| 17 | 1.26 | 29.15 |
| 18 | 0.81 | 11.58 |

EXAMPLE 14

Characterizing the Compound of the Formula (IV)

Empirical formula: $C_{18}H_{32}N_2O_7$
Molecular weight: 388.46
Diastereomeric mixture: 75/25

TABLE 4

NMR-chemical shifts of bengamide (IV), diastereomeric mixture, c = 3.1 mg/ml in DMSO, 300 K.

| Position | $^1$H | $^{13}$C |
|---|---|---|
| 1 | — | 173.45 |
| 2 | 7.55 | — |
| 3 | 3.35/3.02 | 45.05 |
| 4 | 3.74 | 63.48 |
| 4-OH | 4.60 | — |
| 5 | 1.81/1.75 | 34.28 |
| 6 | 1.68/1.64 | 24.25 |
| 7 | 4.32 | 51.18 |
| 8 | 7.77 | — |
| 9 | — | 169.63 |
| 10 | 3.70 | 81.59 |
| 10-OMe | 3.26 | 57.30 |
| 11 | 3.58 | 70.73 |
| 11-OH | 4.47 | — |
| 12 | 3.34 | 72.82 |
| 12-OH | 4.38 | — |
| 13 | 3.97 | 72.47 |
| 13-OH | 4.56 | — |
| 14 | 5.37 | 129.06 |
| 15 | 5.48 | 136.57 |
| 16 | 1.99 | 37.41 |
| 16-Me | 0.93 | 19.90 |
| 17 | 1.26 | 29.15 |
| 18 | 0.81 | 11.58 |

EXAMPLE 15

Characterizing Bengamide E

Empirical formula: $C_{17}H_{30}N_2O_6$
Molecular weight: 358.44

TABLE 5

NMR-chemical shifts of bengamide E, c = 3 mg/ml in DMSO, 300 K.

| Position | $^1$H | $^{13}$C |
|---|---|---|
| 1 | — | 174.01 |
| 2 | 7.91 | — |
| 3 | 3.19/3.06 | 40.56 |
| 4 | 1.74/1.20 | 28.75 |
| 5 | 1.87/1.64 | 27.56 |
| 6 | 1.87/1.36 | 30.72 |
| 7 | 4.39 | 51.27 |

TABLE 5-continued

NMR-chemical shifts of bengamide E,
c = 3 mg/ml in DMSO, 300 K.

| Position | ¹H | ¹³C |
| --- | --- | --- |
| 8 | 7.78 | — |
| 9 | — | 169.60 |
| 10 | 3.69 | 81.61 |
| 10-OMe | 3.25 | 57.30 |
| 11 | 3.56 | 70.74 |
| 11-OH | 4.49 | — |
| 12 | 3.33 | 72.78 |
| 12-OH | 4.38 | — |
| 13 | 3.96 | 72.38 |
| 13-OH | 4.57 | — |
| 14 | 5.38 | 127.68 |
| 15 | 5.58 | 137.85 |
| 16 | 2.24 | 30.08 |
| 17 | 0.95 | 22.27 |
| 18 | 0.95 | 22.17 |

EXAMPLE 16

Characterizing Bengamide F

Empirical formula: $C_{18}H_{32}N_2O_6$
Molecular weight: 372.47

TABLE 6

NMR-chemical shifts of bengamide F,
c = 3 mg/ml in DMSO, 300 K.

| Position | ¹H |
| --- | --- |
| 1 | — |
| 2 | 2.91 |
| 3 | 3.62/3.21 |
| 4 | 1.69/1.33 |
| 5 | 1.84/1.69 |
| 6 | 1.84/1.33 |
| 7 | 4.56 |
| 8 | 7.84 |
| 9 | — |
| 10 | 3.70 |
| 10-OMe | 3.25 |
| 11 | 3.57 |
| 12 | 3.33 |
| 13 | 3.97 |
| 14 | 5.38 |
| 15 | 5.59 |
| 16 | 2.25 |
| 17 | 0.95 |
| 18 | 0.95 |

EXAMPLE 17

Separating the Diastereomers of Compound (II)

The diastereomeric mixture of the compound of formula (II) from example 8 was seperated on a chiral column (AD/H, Daicel, 20×200 mm, 0.5 ml/min, mobile phase: acetonitrile:methanol 4:1+0.1% NH₄Ac). The optical purity was checked on an analytical AD/H column (Daicel) (4.6× 250 mm, 30° C., mobile phase: acetonitrile:methanol 4:1+ 0.1% NH₄Ac, 0.75 ml/min, Rt peak1: 9.9 min, Rt peak2: 10.9 min).

TABLE 7

NMR-chemical shifts of the diastereomers of bengamide (II),
c = 3 mg/ml in DMSO, 300 K.

| | ¹H (A) | ¹H (B) | ¹³C (A) | ¹³C (B) |
| --- | --- | --- | --- | --- |
| 1 | — | — | 173.99 | 173.99 |
| 2 | 7.91 | 7.91 | — | — |
| 3 | 3.19/3.06 | 3.19/3.06 | 40.56 | 40.56 |
| 4 | 1.74/1.20 | 1.74/1.20 | 28.75 | 28.75 |
| 5 | 1.87/1.64 | 1.87/1.64 | 27.55 | 27.55 |
| 6 | 1.87/1.36 | 1.87/1.36 | 30.72 | 30.72 |
| 7 | 4.39 | 4.39 | 51.27 | 51.27 |
| 8 | 7.78 | 7.78 | — | — |
| 9 | — | — | 169.61 | 169.61 |
| 10 | 3.69 | 3.69 | 81.60 | 81.60 |
| 10-OMe | 3.25 | 3.25 | 57.32 | 57.32 |
| 11 | 3.58 | 3.58 | 70.72 | 70.77 |
| 11-OH | 4.46 | 4.47 | — | — |
| 12 | 3.33 | 3.33 | 72.80 | 72.85 |
| 12-OH | 4.36 | 4.36 | — | — |
| 13 | 3.97 | 3.97 | 72.46 | 72.37 |
| 13-OH | 4.56 | 4.56 | — | — |
| 14 | 5.37 | 5.38 | 129.05 | 129.01 |
| 15 | 5.48 | 5.49 | 136.57 | 136.44 |
| 16 | 1.99 | 1.99 | 37.41 | 37.28 |
| 16-Me | 0.93 | 0.92 | 19.90 | 19.86 |
| 17 | 1.26 | 1.26 | 29.15 | 29.06 |
| 18 | 0.81 | 0.82 | 11.58 | 11.48 |

EXAMPLE 18

Cell Proliferation Measurements Performed on Various Tumor Cell Lines

The tumor cell lines Hep-G2 (ATCC No. HB-8065) and COLO 205 (ATCC No. CCL-222) were used for determining the cell proliferation. The cell lines were sown in cell culture medium at the rate of 1000 cells/well [Hep-G2] and, respectively, 3500 cells/well [Colo205] and incubated for 4 hours at 37° C. and 5% $CO_2$.

Medium for Hep-G2: Dulbecco's modified Eagle's medium/Ham's F12 mix (Gibco); NEAA (10%; nonessential amino acids, Gibco), sodium pyruvate (1%, Gibco), L-glutamine (1%, Gibco), fetal calf serum (5%; PAA)].

Medium for COLO 205: RPMI 1640 (Gibco), L-glutamine (1%, Gibco), HEPES (1%, Gibco), fetal calf serum (10%, PAA).

After 4 hours, compounds (II), (III) and (IV) and bengamides E and F, dissolved in DMSO/cell culture medium, were added at various dilutions and the mixtures were incubated for 72 hours at 37° C. and 5% $CO_2$. The intracellular content of ATP was determined using the test reagent CellTiterGlo (Promega).

The results of the cell proliferation tests are reported in table 1.

What is claimed is:
1. A compound of the formula (I),

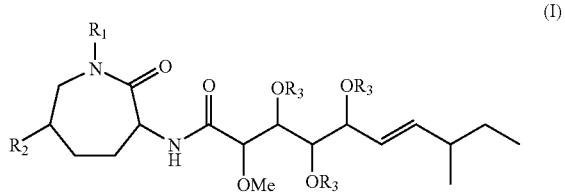

wherein
R₁ is H or (C₁–C₆)-alkyl,
R₂ is H or OH, and
R₃ is H or —C(=O)—(C₁–C₆)-alkyl,
or a physiologically tolerated salt thereof.

2. The compound according to claim 1, wherein R₁ is H or methyl.

3. The compound according to claim 1, wherein R₃ is H.

4. The compound according to claim 2, wherein R₃ is H.

5. The compound according to claim 1, having the formula (II)

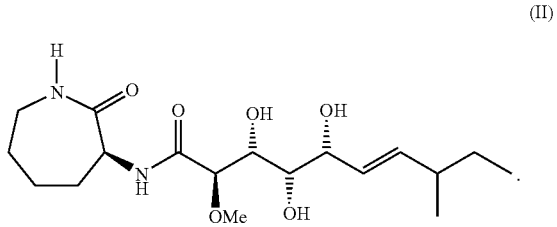

(II)

6. The compound according to claim 2, having the formula (II).

7. The compound according to claim 3, having the formula (II).

8. The compound according to claim 4, having the formula (II).

9. The compound according to claim 1, having the formula (III)

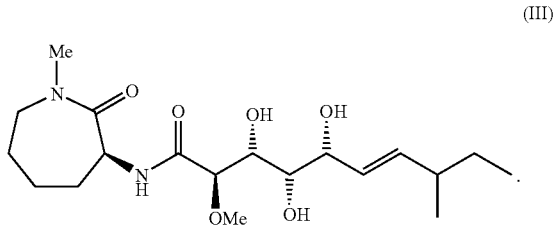

(III)

10. The compound according to claim 2, having the formula (III).

11. The compound according to claim 3, having the formula (III).

12. The compound according to claim 4, having the formula (III).

13. The compound according to claim 1, having the formula (IV)

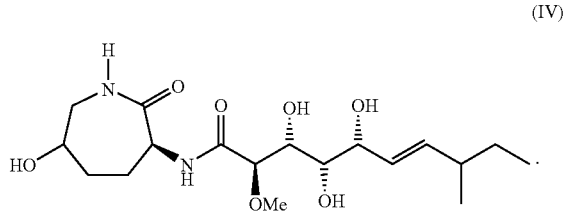

(IV)

14. The compound according to claim 2, having the formula (IV).

15. The compound according to claim 3, having the formula (IV).

16. The compound according to claim 4, having the formula (IV).

17. A method of treating a cancer, selected from the group consisting of breast cancer, glioblastoma, colon cancer, lung cancer, prostate cancer and leukemia, comprising administering to a subject in need thereof, a therapeutically effective amount of a compound according to claim 1.

18. A method of treating a cancer, selected from the group consisting of breast cancer, glioblastoma, colon cancer, lung cancer, prostate cancer and leukemia, comprising administering to a subject in need thereof, a therapeutically effective amount of a compound according to claim 2.

19. A method of treating a cancer, selected from the group consisting of breast cancer, glioblastoma, colon cancer, lung cancer, prostate cancer and leukemia, comprising administering to a subject in need thereof, a therapeutically effective amount of a compound according to claim 3.

20. A method of treating a cancer, selected form the group consisting of breast cancer, glioblastoma, colon cancer, lung cancer, prostate cancer and leukemia, comprising administering to a subject in need thereof, a therapeutically effective amount of a compound according to claim 4.

21. A method of treating a cancer, selected form the group consisting of breast cancer, glioblastoma, colon cancer, lung cancer, prostate cancer and leukemia, comprising administering to a subject in need thereof, a therapeutically effective amount of a compound according to claim 5.

22. A method of treating a cancer, selected from the group consisting of breast cancer, glioblastoma, colon cancer, lung cancer, prostate cancer and leukemia, comprising administering to a subject in need thereof, a therapeutically effective amount of a compound according to claim 9.

23. A method of treating a cancer, selected from the group consisting of breast cancer, glioblastoma, colon cancer, lung cancer, prostate cancer and leukemia, comprising administering to a subject in need thereof, a therapeutically effective amount of a compound according to claim 13.

24. A pharmaceutical composition comprising at least one compound of formula (I) or of a physiologically tolerated salt thereof, according to claim 1; in combination with at least one pharmaceutically suitable carrier substance.

25. The pharmaceutical composition comprising at least one compound of formula (I) or of a physiologically tolerated salt thereof, according to claim 2; in combination with at least one pharmaceutically suitable carrier substance.

26. The pharmaceutical composition comprising at least one compound of formula (I) or of a physiologically tolerated salt thereof, according to claim 3; in combination with at least one pharmaceutically suitable carrier substance.

27. The pharmaceutical composition comprising at least one compound of formula (I) or of a physiologically tolerated salt thereof, according to claim 4; in combination with at least one pharmaceutically suitable carrier substance.

28. The pharmaceutical composition comprising at least one compound of formula (II) or of a physiologically tolerated salt thereof, according to claim 5; in combination with at least one pharmaceutically suitable carrier substance.

29. The pharmaceutical composition comprising at least one compound of formula (III) or of a physiologically tolerated salt thereof, according to claim 9; in combination with at least one pharmaceutically suitable carrier substance.

30. The pharmaceutical composition comprising at least one compound of formula (IV) or of a physiologically tolerated salt thereof, according to claim 13; in combination with at least one pharmaceutically suitable carrier substance.

* * * * *